United States Patent [19]

Wiley

[11] 4,252,949
[45] Feb. 24, 1981

[54] MONOESTERS OF PYRAZINETETRACARBOXYLIC ACID

[76] Inventor: Richard H. Wiley, 8 Roosevelt Cir., Palo Alto, Calif. 94306

[21] Appl. No.: 71,695

[22] Filed: Aug. 31, 1979

[51] Int. Cl.³ .......................................... C07D 241/12
[52] U.S. Cl. .................................................. 544/406
[58] Field of Search ........................................ 544/406

[56] References Cited

U.S. PATENT DOCUMENTS 3,915,974  10/1975  Cairncress ............................. 54/406

FOREIGN PATENT DOCUMENTS 2412521  10/1974  Fed. Rep. of Germany .

*Primary Examiner*—José Tovar

[57] ABSTRACT

Previously unknown and undescribed long chain (C-12 to C-18) monoesters of pyrazinetetracarboxylic acid have been prepared and shown to be effective surface active agents useful as detergents, sequestrants, and chelating agents for extractive metallurgy.

2 Claims, No Drawings

MONOESTERS OF PYRAZINETETRACARBOXYLIC ACID

BACKGROUND OF THE INVENTION

No monoesters of pyrazinetetracarboxylic acid have been prepared or described. The normal product of the acid-catalyzed esterification of pyrazinetetracarboxylic acid is the tetraester and previous descriptions of such preparations give no indication of a method for the preparation of a mono ester or any characteristics of partial esterification products.

SUMMARY OF THE INVENTION

The previously undesribed, uncatalyzed reaction of pyrazinetetracarboxylic acid with alcohols gives the monoesters and the long chain (C-ten to C-eighteen) mono esters thus prepared are surface active agents useful as detergents, sequestrants, and chelating agents for extractive metallurgy. The copper chelate is formed from dilute acid solutions of cupric ions and decomposed by strong acid.

DESCRIPTION OF THE INVENTION

Pyrazinetetracarboxylic acid, obtained by the permanganate oxidation of phenazine or tetramethyl pyrazine, is a well-known material. It is reacted with excess long chain primary alcohol, such as decyl, dodecyl, tetradecyl, cetyl, or octadecyl having ten to eighteen carbon atoms, by warming and heating. No added esterification catalyst of the usual type, such as mineral acid or sulfonic acid, is required. Excess alcohol is desirable but is not essential. The product is the monoester. The tetracarboxylic acid, which is a strong acid of $pK_a$ about 0.9, functions as an autocatalyst until converted to the monoester which is no longer sufficiently strong to autocatalyze further esterification. The monoester product is purified by physical methods, such as recrystallization or by chromatography, or by chemical methods, including extraction of the unreacted excess alcohol, if any is used, from the monoester with a suitable solvent, such as ether or ligroin. The crude or purified mono esters give soapy solutions in aqueous alkali which emulsify solids; They sequester calcium ions preventing their precipitation at pH above 7; and they form oil soluble chelates of metals such as copper from which the metal can be separated with strong acid.

The invention is further described in the following examples.

EXAMPLE 1

Carefully dried, recrystallized pyrazinetetracarboxylic acid (100 mg) is refluxed under nitrogen for ten minutes with 1 ml of dodecanol-1. The liquid layer is decanted and vacuum dried at 100° and 2 mm for two hours. The product consists of a 15±5% solution of the monododecyl ester in dodecanol. Anal.: C, 75.42%; H, 12.45%; N, 1.2%. The product gives a foamy soapy solution in 2 N sodium hydroxide which emulsifies carbon black.

EXAMPLE 2

Example 1 is repeated using 100 mg of octadecanol-1. The product is vacuum dried at 100° and 5 mm for seven hours. The product is a 21±6% solution of the monooctadecyl ester of pyrazinetetracarboxylic acid in octadecanol. Anal.: C, 76.19; H, 1312%; N, 1.55%.

EXAMPLE 3

Example 1 is repeated using 185 mg of cetyl alcohol and 255 mg of recrystalized, dried pyrazinetetracarboxylic acid. The mixture is heated under nitrogen at 100° for ten minutes, cooled, and extracted with ether. The ether extracts on evaporation deposited a solid, mp. over 100°, which consists of a 42±4% solution of the mono cetyl ester of pyrazinetetracarboxylic acid in cetyl alcohol. Anal: C, 71.40%; H,11.35%; N, 2.37%.

EXAMPLE 4

Example 2 is repeated using 100 mg of decyl alcohol. The product is a solution of the monodecyl ester in decyl alcohol.

EXAMPLE 5

The copper chelate of the monooctadecyl ester of pyrazine tetracarboxylic acid is obtained by adding a 1% cupric chloride solution to an ethanol-ligroin solution of the monoester. A blue colored organic phase is formed and the aqueous phase decolorized. Shaking with 6 N sulfuric acid redissolves the copper in the aqueous phase as a blue solution.

EXAMPLE 6

The 42% solution of the monoester obtained as in example 3 is separated into its consituents by chromatography over silica gel. The pure monocetyl ester of pyrazinetetracarboxylic acid is obtained.

What is claimed is:
1. A mono alkyl ester of pyrazinetetracarboxylic acid having ten to eighteen carbon atoms in the carbon chain.
2. Monocetyl pyrazinetetracarboxylate.

* * * * *